United States Patent [19]

Greene et al.

[11] Patent Number: 5,556,839
[45] Date of Patent: Sep. 17, 1996

[54] FORM II DIRITHROMYCIN

[75] Inventors: James M. Greene; Holly M. Hankins, both of Indianapolis; Gregory A. Stephenson, West Lafayette, all of Ind.

[73] Assignee: Eli Lilly and Company, Indianapolis, Ind.

[21] Appl. No.: 369,980

[22] Filed: Jan. 9, 1995

Related U.S. Application Data

[63] Continuation of Ser. No. 904,781, Jun. 26, 1992, abandoned, which is a continuation-in-part of Ser. No. 692,842, Apr. 29, 1991, abandoned.

[51] Int. Cl.$^6$ .................................................. C07H 17/08
[52] U.S. Cl. ........................... 514/29; 536/7.2; 536/7.4; 424/115; 424/464
[58] Field of Search ................... 536/7.2, 7.4; 514/29; 424/115, 464

[56] References Cited

U.S. PATENT DOCUMENTS

| | | | |
|---|---|---|---|
| 4,048,306 | 9/1977 | Maier et al. | 514/29 |
| 4,265,900 | 5/1981 | Rasmussen et al. | 514/392 |
| 4,743,593 | 5/1988 | Hunt | 514/29 |
| 4,755,385 | 7/1988 | Etienne et al. | 424/154 |

OTHER PUBLICATIONS

Luger, Peter et al., *9 Journal of Crystal and Molecular Structure* 329–338 (1979).
Allen, P. V. et al., *67 Journal of Pharmaceutical Sciences*, 1087–1092 (1978).
Chemical Abstracts 85:25320x, p. 251 (1976).
Pelizza, G. et al., *31 Farmaco Ed. Sc.* 254–263 Article referred to by Chemical Abstracts 85:25320x, above (CC).
Egutkin, H. L., et al., Khim.–Farm. Zh., 18(7), 858–61, 1984.
J. Firl, et al., *Journal of Antibiotics*, vol. XLIII, No. 10, pp. 1271–1277, Oct. 1990, Tokyo, Japan.
European Search Report.

*Primary Examiner*—Elli Peselev
*Attorney, Agent, or Firm*—MaCharri Vorndran-Jones

[57] ABSTRACT

The invention provides Form II dirithromycin, a novel polymorph of dirithromycin. Also disclosed are the acetone, 1-butanol, 1-propanol, and 2-propanol solvates of dirithromycin, which provide an efficient means for preparing and isolating Form II. Processes for preparing and isolating Form II dirithromycin from these solvates or from Form I dirithromycin are provided. A process for obtaining Form II dirithromycin from non-solvated dirithromycin is also provided. Another aspect of the invention is an improved tablet containing Form II dirithromycin as the active ingredient.

5 Claims, No Drawings

FORM II DIRITHROMYCIN

CROSS REFERENCE

This application is a continuation of application Ser. No. 07/904,781 filed on Jun. 26, 1992, now abandoned which is a continuation-in-part of 07/692,842 filed Apr. 29, 1991, now abandoned.

BACKGROUND OF THE INVENTION

This invention concerns semi-synthetic pharmaceutical chemistry, and relates to novel solvate forms of a macrolide antibiotic. More particularly, this invention provides the acetone, 1-propanol, 2-propanol, and 1-butanol solvates of the macrolide antibiotic dirithromycin. The stable solvates provide an efficient method of isolating pharmaceutically acceptable dirithromycin in excellent purity and yield.

Dirithromycin, also known as 9-deoxo-11-deoxy- 9,11-(imino[2-(2-methoxyethoxy)ethylidene]oxy)-(9S,16R)-erythromycin, is a macrolide antibiotic derived from erythromycin. The antibiotic is described in Example 9 of U.S. Pat. No. 4,048,306 of Boehringer Ingelheim. The spectrum of activity of this antibiotic approximates that of erythromycin; however, dirithromycin has the distinct advantageous property of providing high concentrations of antibiotic activity in the tissues while the plasma levels of the antibiotic remain low. To date, however, purification of this antibiotic has been difficult and somewhat inefficient.

The formation of solvates is known to be a highly individualistic effect. Dirithromycin is known to crystallize as a solvated crystal from acetonitrile; however, the acetonitrile solvate of dirithromycin is known to be unstable. See P. Lugar, R. Maier, Molecular Structure of 9-deoxy-11-deoxy-9-11-(imino (2-(2methoxyethoxy)ethylidene)oxy)-( 9S) -erythromycin, a new erythromycin derivative, 9 *Journal of Crystal and Molecular Structure* 329 (1979).

Applicants have discovered that dirithromycin exists in two forms which are distinguishable by x-ray powder diffractometry. The two forms are designated Form I and Form II. Dirithromycin prepared by the method described in U.S. Pat. No. 4,048,306 is produced in the form of a polymorph which is hereinafter referred to as "Form I". Form I dirithromycin has the following x-ray powder diffraction pattern, wherein d represents the interplanar spacing and $I/I_o$ the relative intensity:

| d (Å) | $I/I_o$ |
|---|---|
| 11.28 | 1.00 |
| 9.81 | 0.35 |
| 8.53 | 0.76 |
| 7.67 | 0.23 |
| 7.12 | 0.02 |
| 6.94 | 0.02 |
| 6.66 | 0.10 |
| 6.39 | 0.09 |
| 5.97 | 0.21 |
| 5.65 | 0.69 |
| 5.42 | 0.67 |
| 5.18 | 0.23 |
| 4.83 | 0.31 |
| 4.64 | 0.07 |
| 4.43 | 0.40 |
| 4.26 | 0.17 |
| 4.14 | 0.05 |
| 4.06 | 0.15 |
| 3.86 | 0.15 |
| 3.76 | 0.17 |
| 3.62 | 0.10 |
| 3.50 | 0.08 |
| 3.43 | 0.03 |
| 3.35 | 0.07 |
| 3.04 | 0.07 |
| 2.95 | 0.02 |
| 2.88 | 0.02 |
| 2.84 | 0.02 |
| 2.71 | 0.03 |
| 2.66 | 0.02 |
| 2.58 | 0.03 |

Unfortunately, Form I is metastable and is therefore not well suited for use in pharmaceutical formulations such as tablets. However, surprisingly, and in accordance with the invention, it has now been discovered that the second polymorph of dirithromycin, hereinafter referred to as "Form II", is stable, and therefore is well adapted for use in pharmaceutical formulations such as tablets.

The new purified Form II dirithromycin had the following x-ray powder diffraction pattern, wherein d represents the interplanar spacing and $I/I_o$ the relative intensity:

| d (Å) | $I/I_o$ |
|---|---|
| 14.17 | 0.02 |
| 11.96 | 0.27 |
| 10.43 | 0.11 |
| 9.65 | 1.00 |
| 8.86 | 0.84 |
| 8.18 | 0.54 |
| 7.07 | 0.33 |
| 6.99 | 0.10 |
| 6.84 | 0.21 |
| 6.59 | 0.03 |
| 6.24 | 0.05 |
| 6.07 | 0.29 |
| 5.97 | 0.19 |
| 5.77 | 0.06 |
| 5.54 | 0.36 |
| 5.50 | 0.47 |
| 5.45 | 0.26 |
| 5.13 | 0.22 |
| 5.11 | 0.29 |
| 4.75 | 0.47 |
| 4.72 | 0.42 |
| 4.50 | 0.62 |
| 4.44 | 0.31 |
| 4.24 | 0.20 |
| 4.20 | 0.05 |
| 4.11 | 0.17 |
| 4.09 | 0.18 |
| 3.92 | 0.14 |
| 3.87 | 0.12 |
| 3.83 | 0.12 |
| 3.73 | 0.06 |
| 3.55 | 0.08 |
| 3.49 | 0.15 |
| 3.46 | 0.07 |
| 3.42 | 0.11 |
| 3.33 | 0.05 |
| 3.17 | 0.04 |
| 3.11 | 0.02 |
| 2.96 | 0.04 |
| 2.83 | 0.02 |
| 2.74 | 0.04 |
| 2.57 | 0.03 |

The Form I crystal can be isolated via the acetonitrile solvate of dirithromycin and exposure of the solvate to air or vacuum drying. The method of preparing Form I dirithromycin is described in U.S. Pat. No. 4,048,306 of Boehringer Ingelheim, which is hereby incorporated by reference.

The disadvantage of Form I is that it is metastable, i.e. it gradually converts to a mixture containing the second crystal type, Form II, with time. This conversion is accelerated with increased temperature. The conversion of crystalline Form I to Form II occurs at temperatures from about 80° C. to about 130° C.

It is desirable to isolate the pure Form II crystal of dirithromycin to assure uniformity of product. The method of this invention provides isolated Form II dirithromycin of greatly improved quality via a convenient, efficient, and ecologically friendly isolation process.

SUMMARY OF THE INVENTION

This invention provides new solvates of dirithromycin, i.e. the acetone, 1-butanol, 1-propanol, and 2-propanol solvate forms of dirithromycin. The invention also provides purified Form II dirithromycin, having a typical x-ray powder diffraction pattern as described supra,. Also provided are processes for isolating Form II dirithromycin in purified form. One process comprises slurrying one of the solvates of this invention in a solvent comprising from about 40% to about 100% water with stirring to produce purified solid, Form II dirithromycin.

The invention further provides a process for isolating Form II dirithromycin which comprises slurrying Form I dirithromycin in a solvent comprising from about 80% to about 100% water, wherein the solvent temperature is about 40° to about 80° C., with stirring to produce solid, purified Form II dirithromycin.

The invention also provides a process for obtaining Form II dirithromycin which comprises dissolving a "dirithromycin intermediate" selected from a dirithromycin solvate of this invention, amorphous dirithromycin, or Form I dirithromycin, in ethyl acetate or toluene, at a temperature of from about ambient temperature to about 80° C., with mixing, to produce purified Form II dirithromycin.

In another embodiment of the invention, there is provided a pharmaceutical formulation containing purified Form II dirithromycin as an active ingredient. The formulation, most preferably in tablet form, will also, of course, contain one or more pharmaceutically-acceptable excipients, such as binders, lubricants, disintegrants, fillers, etc.

DETAILED DESCRIPTION OF THE INVENTION

This invention provides purified Form II dirithromcyin. Since Form II dirithromycin is to be used as a pharmaceutical product it should be in a pharmaceutical state of purity. For stability purposes, purified Form II should be substantially free from Form I. Preferably, Form II should be associated with less than 10% of Form I; more preferably it should contain less than 5%; and most preferably it should contain less than 2%.

This invention also provides efficient processes to prepare Form II dirithromycin. The Form II dirithromycin may be prepared via the acetone, 1-butanol, 1-propanol, or 2-propanol solvates of dirithromycin or from Form I. These solvates of dirithromycin, are novel compounds that facilitate the isolation of pharmaceutically acceptable dirithromycin Form II by removing impurities, as demonstrated by HPLC chromatogram.

The novel solvates may be formed by dissolving dirithromycin in a solvent comprised of from about 0% to 80% aqueous solvent and from about 20% to 100% non-aqueous solvent. The non-aqueous solvent used corresponds to the desired dirithromycin solvate product. Thus, for example, when the acetonate is desired, the solvent mixture would be an aqueous solvent and acetone. The temperature of the mixture should be from ambient temperature to about 90° C. The mixture should be stirred for about 20 minutes or more. The reaction time required will vary with the temperature of the reaction, pressure, and with the completion of reaction desired. The progress of the reaction may be followed by x-ray powder diffraction techniques.

The particular techniques used to obtain all x-ray powder diffraction patterns herein used a Nicolet 12V powder diffractometer equipped with a graphite monochrometer with copper radiation of 1=1.5418/angstroms. It will be understood that the intensity values may vary due to sample preparation and instrument variations. Therefore, those skilled in the art will appreciate that the d-spacings constitute the essence of the diffraction pattern.

Preferred reaction conditions for preparing the solvates include a reaction temperature of about 50° C. to about 92° C. with a reaction time of about 30 minutes or longer. The solid solvate form of dirithromycin may be crystallized from the solution by conventional methods, including cooling or chilling, crystal seeding, evaporation of a portion of the solution, or by addition of water or organics, such as hexane, to encourage crystallization. The solid may be isolated by conventional methods including filtration and centrifugation. The isolated solid may be washed with solvent to improve purity. The solvate may be dried or used as the wet cake for subsequent reactions or isolation procedures.

Alternatively, the solvate formation may be achieved during the formation of dirithromycin. This process comprises dissolving 2-(2-methoxyethoxy)acetaldehyde or its equivalent in the form of a hydrate, or hemiacetal, in acetone, 1-butanol, 1-propanol, or 2-propanol. The solvent is chosen based on the solvate form of dirithromcyin desired. 9(S)-erythromycylamine is added to the reaction mixture with stirring. A preferred concentration of the erythromycylamine is from about 0.2 molar to about 0.7 molar. The concentration of the acetaldehyde and erythromycylamine may vary widely; however, the reaction is most efficient when the molar ratio is greater than 1.1 moles of aldehyde per 1 mole erythromycylamine. The reaction is stirred from about 30 minutes to about 20 hours. The reaction time should be based on the degree of completion desired, and may be run for a longer period of time. The reaction may be run under nitrogen atmosphere. Crystallization of the solvate may be completed by conventional methods including, but not limited to cooling, crystal seeding, and solvent evaporation. The percent recovery may be enhanced by allowing crystallization to proceed overnight and by stirring in an ice bath. The solid may be isolated by conventional methods. The isolated solid may be washed with chilled solvent to improve purity. The solid may be dried or used as the wet cake, as mentioned above.

The acetone, 1-butanol, 1-propanol, and 2-propanol solvate forms of dirithromycin may be used to prepare and isolate Form II dirithromcyin. The potency of the Form II dirithromycin product may be enhanced through the use of solvates with low total related substance values. Most preferably, a solvate formed by dissolving dirithromcyin in solvent, as described above, is used for the Form II dirithromycin preparation and isolation. The process comprises slurrying one of these solvates in a solvent comprised of from about 70% to 100% aqueous solvent and from about 0% to 30% non-aqueous solvent. The non-aqueous solvent corresponds to the solvate form being used and should be selected from acetone, 1-butanol, 1-propanol, and 2-propanol. A preferred solvent contains from about 80% to about 100% water. A most preferred solvent contains from about 95% to about 100% water.

The slurry is stirred at from about ambient temperature to about 80° C. for about 2.5 hours or more. The temperature may vary based on pressure and desired speed of X-8376A-11reaction. A preferred temperature is from about 40° C. to about 80° C. A more preferred temperature is from about 40° C. to about 50° C. The completion of reaction may be monitored by x-ray powder diffractometry techniques and differential thermal analysis. The solid Form II dirithromycin may be isolated by conventional methods including vacuum filtration, simple filtration, or centrifugation. The solid may be washed with water or a solution of one of the four solvents with water and dried.

In the second process of this invention, Form II dirithromycin may be prepared from Form I dirithromycin. Form I dirithromycin is slurried and heated, and Form II is prepared and isolated as in the process utilizing the solvate form of dirithromycin above. The preferred temperature range is about 40° C. to about 80° C. The most preferred range is from about 60° C. to about 80° C. The preferred solvent comprises from about 95% to about 100% water. The solid product of the process is the stable Form II dirithromcyin which may be dried in a vacuum oven or by other known methods.

In the third process of this invention, Form II may be prepared from a dirithromycin intermediate selected from non-solvated or amorphous dirithromycin, a dirithromycin solvate of this invention or Form I dirithromycin by dissolving the intermediate in ethyl acetate or toluene. The preferred solvent is ethyl acetate. The preferred concentration of dirithromycin intermediate is from about 0.10 molar to about 0.28 molar. The concentration may vary with temperature, pressure, time, and degree of agitation. The preferred temperature is from about 60° C. to about 80° C. Crystallization of Form II dirithromycin may be completed by conventional methods including solvent evaporation, seeding, cooling, and addition of an antisolvent such as n-heptane or n-octane. The solid may be isolated by conventional methods. The isolated solid may be washed with antisolvent to improve purity.

Effective drying methods include vacuum oven drying, air oven or simple vacuum desiccator drying. The solvates are stable at ambient temperature and will tolerate vacuum drying. When vacuum oven drying is used, one must exercise caution to avoid breaking the solvate. Preferred drying conditions for the acetone solvate are about 40° C. to about 50° C. vacuum oven drying and about 30° C. to about 40° C. vacuum oven drying for the isopropanol solvate. Preferred drying conditions for the Form II dirithromycin are vacuum oven drying at temperatures from about 45° C. to about 55° C.

It will be understood that the concentration of dirithromycin is not a critical factor in the preparation of the solvate or in the preparation of Form II dirithromcyin. A preferred concentration range for dirithromcyin in the solvate formation is from about 0.1 to about 0..2 molar. A preferred concentration range of solvate to be used in the isolation of Form II dirithromycin is from about 0.1 molar to about 0.2 molar.

The solvates of this invention are true solvates having a fixed composition of about 1 solvent molecule per molecule of dirithromycin. The solvates of this invention are particularly useful because they are stable at ambient conditions.

They have been found to be very useful in the purification of dirithromcyin and as intermediates for subsequent reactions.

The following examples further illustrate the invention. The potency values reported in these examples represent the purity of the product with respect to an anhydrous standard. Due to 5 to 10% solvent content in the sample, the reported potency values are less than the potency of the standard. The values for total related substances (TRS) and potency were determined by HPLC analysis utilizing UV detection at 205 nm.

The following table summarizes the 13C NMR assignments for dirithromycin (Form I) and the four new dirithromycin solvates (propanol, iso-propanol, n-butanol, and acetone solvates). The NMR spectra of the dirithromycin solvates were recorded at 75.4 MHz at a concentration of 100 mg/mL in deuterated chloroform. The shifts are referenced to chloroform-d at 77.00 ppm. The spectra of dirithromycin were recorded at 75.4 MHz at a concentration of 50 mg/mL in deuterated chloroform (chloroform-d) with 1% tetramethylsilane. Chemical shifts are referenced to chloroform-d at 77.00 ppm. Note that a numbered structure follows the NMR spectra table.

TABLE

| Assignment | Dirithromycin | Propanol | Iso-propanol | n-butanol | Acetone |
| --- | --- | --- | --- | --- | --- |
| 1 | 176.99 | 176.95 | 176.95 | 176.95 | 176.94 |
| 2 | 44.39 | 44.40 | 44.40 | 44.40 | 44.40 |
| 3 | 76.88 | 76.81 | 76.82 | 76.81 | 76.81 |
| 4 | 44.58 | 44.51 | 44.52 | 44.51 | 44.52 |
| 5 | 79.17 | 79.07 | 79.08 | 79.07 | 79.08 |
| 6 | 74.53 | 74.51 | 74.51 | 74.52 | 74.49 |
| 7 | 39.28 | 39.19 | 39.20 | 39.19 | 39.21 |
| 8 | 29.39 | 29.33 | 29.34 | 29.33 | 29.34 |
| 9 | 66.03 | 65.95 | 65.96 | 65.96 | 65.96 |
| 10 | 27.57 | 27.51 | 27.52 | 27.51 | 27.51 |
| 11 | 72.75 | 72.74 | 72.74 | 72.76 | 72.71 |
| 12 | 74.37 | 74.31 | 74.32 | 74.32 | 74.31 |
| 13 | 76.44 | 76.37 | 76.37 | 76.37 | 76.37 |
| 14 | 21.41 | 21.34 | 21.34 | 21.34 | 21.35 |
| 15 | 11.23 | 11.17 | 11.18 | 11.17 | 11.18 |
| 16 | 82.81 | 82.54 | 82.66 | 82.63 | 82.73 |
| 17 | 71.99 | 71.90 | 71.91 | 71.90 | 71.93 |
| 18 | 72.90 | 72.84 | 72.85 | 72.85 | 72.84 |
| 19 | 71.07 | 70.95 | 70.96 | 70.94 | 70.99 |
| 20 | 49.21 | 49.15 | 49.16 | 49.16 | 49.15 |
| 21 | 12.91 | 12.85 | 12.86 | 12.85 | 12.86 |
| 22 | 9.01 | 8.95 | 8.96 | 8.95 | 8.96 |
| 23 | 24.75 | 24.67 | 24.68 | 24.67 | 24.69 |
| 24 | 20.77 | 20.74 | 20.74 | 20.74 | 20.73 |
| 25 | 14.15 | 14.09 | 14.10 | 14.10 | 14.10 |
| 26 | 14.85 | 14.83 | 14.83 | 14.84 | 14.81 |
| 1' | 101.00 | 100.94 | 100.94 | 100.94 | 100.93 |
| 2' | 71.09 | 71.04 | 71.04 | 71.05 | 71.03 |
| 3' | 65.01 | 64.91 | 64.93 | 64.91 | 64.94 |
| 4' | 28.92 | 28.90 | 28.89 | 28.91 | 28.87 |
| 5' | 69.43 | 69.36 | 69.37 | 69.37 | 69.37 |
| 6' | 21.09 | 21.03 | 21.03 | 21.03 | 21.03 |
| N(CH$_3$)$_2$ | 40.40 | 40.34 | 40.35 | 40.34 | 40.34 |
| 1" | 94.35 | 94.30 | 94.31 | 94.31 | 94.30 |
| 2" | 34.46 | 34.39 | 34.40 | 34.40 | 34.40 |
| 3" | 72.72 | 72.68 | 72.68 | 72.68 | 72.68 |
| 4" | 78.47 | 78.41 | 78.42 | 78.41 | 78.42 |
| 5" | 65.77 | 65.72 | 65.73 | 65.73 | 65.72 |
| 6" | 18.39 | 18.33 | 18.34 | 18.33 | 18.34 |
| 7" | 21.86 | 21.83 | 21.83 | 21.83 | 21.83 |
| 8" | 58.99 | 58.93 | 58.93 | 58.93 | 58.94 |
| solvate 1 | | 10.8 | 25.27 | 13.78 | 30.78 |
| solvate 2 | | 25.8 | 64.16 | 18.85 | 206.62 |
| solvate 3 | | 64.43 | | 34.80 | |
| solvate 4 | | | | 62.48 | |

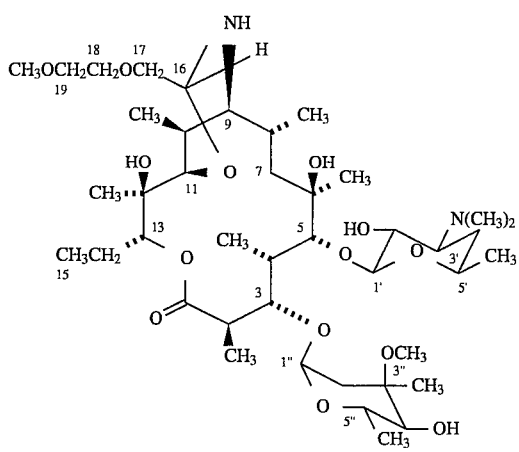

Dirithromycin is an effective antibiotic and has considerable advantages over other macrolide antibiotics since it need only be administered once a day. However, some care is needed in the design of orally acceptable formulations since the compound is sensitive to acidic media such as present in the stomach. In this context, reference is made to U.S. Pat. No. 4,755,385.

Appropriate pharmaceutical formulations are in the form of a solid preparation containing a basic excipient. The basic excipients used may be, either on their own or combined with one another, oxides, hydroxides, or carbonates of magnesium or calcium, hydrogen carbonates or hydroxides of sodium or potassium. Typical basic excipients include magnesium hydroxide, magnesium carbonate, magnesium hydrogen carbonate, calcium hydroxide, calcium carbonate, sodium hydrogen carbonate, magnesium oxide, potassium carbonate, and sodium carbonate. Of course, other excipients, such as binders, disintegrants, and lubricants may be added. The solid pharmaceutical preparations include tablets, pellets, or granules. A syrup can be produced from the granule preparation.

General methods of preparing pharmaceutical formulations containing dirithromycin are disclosed in U.S. Pat. No. 4,755,385. In substance, the process of manufacture involves the admixture of Form II dirithromycin with the necessary pharmaceutically acceptable carriers followed by compression into tablets or pellets and, optionally, coating with a layer resistant to gastric juices. The preferred preparation is the tablet formulation of this invention. The most preferred preparation is a tablet with a coating layer resistant to gastric juices, i.e. an "enteric coating". The nature of such coatings are well known to those skilled in the art.

EXAMPLE 1

Acetone Solvate of Dirithromycin

A 4.9 g portion of 2-(2-methoxyethoxy)acetaldehyde was dissolved in 60 mL reagent grade acetone. A 20.0 g portion of (9S)-erythromycylamine A was added to the reaction mixture with stirring. The mixture was stirred for 2 hours in a nitrogen atmosphere at room temperature. The mixture was seeded with dirithromycin crystals and stirred overnight at room temperature.

The reaction mixture was stirred for 1 hour in an ice bath. The solid was isolated by filtration and was washed with 20.0 mL of cold acetone. The wet cake of solid was resuspended in 40 mL of acetone. The reslurried mixture was stirred at about 0° C. to about 5° C. for 1 hour. The solid was isolated by filtration and washed with 20.0 mL of cold acetone. The solid was dried in a vacuum oven at 50° C. overnight. The product was identified as the acetone solvate of dirithromycin by x-ray powder diffractometry and NMR spectroscopy. The total yield of the compound was 17.68 g (77.8%)

Potency: 91.6%

TRS: 2.9% (reduced from 12.2% before resuspension).

EXAMPLE 2

Acetone Solvate of Dirithromycin

A 10.0 g sample of dirithromycin was added to a 30 mL solvent mixture comprised of 90% acetone and 10% water. The reaction mixture was heated to reflux and 10 additional milliliters of solvent were added to dissolve remaining solids. The clear, colorless solution was stirred while adding 68 mL of 58-60° C. water. The reaction mixture was stirred 0.5 hour at about 58° C. The mixture was allowed to cool to room temperature (about 2 hours). The cooled mixture was placed in an ice bath and stirred for 2 hours. The solid was isolated by filtration, and rinsed with a 20 mL chilled mixture of 67% water: 33% acetone. The isolated solid was dried in vacuo at 40° C. overnight. The product was identified as the acetone solvate of dirithromycin by x-ray powder diffractometry.

Total yield: 87.1%

Potency: 87.3%

TRS: 1.92% (reduced from 4.51% in the starting dirithromycin)

EXAMPLE 3

Acetone Solvate of Dirithromycin

A 10.0 g sample of dirithromycin was added to a 55 mL solvent mixture comprised of 90% acetone and 10% water. The reaction mixture was heated and 23 mL of solvent was distilled away. The clear, colorless solution was stirred at 58°–60° C. for 0.5 hour. A 52 mL portion of water was added in small aliquots over the 30 minutes of heated stirring. The reaction mixture was allowed to cool to room temperature. The cooled mixture was placed in an ice bath and stirred for 0.75 hours. The solid was isolated by filtration and rinsed with a 20 mL chilled mixture of 67% water: 33% acetone. The isolated solid was dried in vacuo at 40° C. overnight. The product was identified as the acetone solvate of dirithromycin by x-ray powder diffractometry.

Total yield: 92.6%

Potency: 89.0%

TRS: 1.93% (reduced from 4.51% in starting dirithromycin)

EXAMPLE 4

Acetone Solvate of Dirithromycin

A 9 g portion of Form I dirithromycin was added to 27 mL acetone. The reaction mixture was heated to 50° C. and stirred for 2.5 hours. The reaction mixture was allowed to cool to 5° C. and the mixture was stirred for 40 minutes at 5° C. The solid was isolated by filtration and washed with 20 mL of 5° C. acetone. The sample was dried in a vacuum oven at 50° C. The product was identified as the acetone solvate of dirithromycin by x-ray powder diffractometry.

Yield: 77%

EXAMPLE 5

1-Propanol Solvate of Dirithromycin

A 5 g portion of dirithromycin was added to a solvent mixture comprised of 5 mL water and 23 mL 1-propanol. The solution was heated to boiling and allowed to boil until the reaction volume was 10 mL. Dirithromycin seed crystals were added to the mixture with stirring. The reaction mixture was allowed to cool to room temperature and 20 mL of water were added to the sample with stirring. The solid was isolated by filtration and washed with 3 washes, each of 50 mL water. The sample was dried in a vacuum dessicator. The product was identified as the 1-propanol solvate by x-ray powder diffractometry and NMR spectroscopy.

EXAMPLE 6

1-Propanol Solvate of Dirithromycin

A 10.0 g sample of dirithromycin was dissolved in a solvent mixture comprised of 18 mL of 1-propanol and 12 mL of water. The solvent was heated to about 50° C. to dissolve remaining solids. The solution was stirred at about 50° C. for 0.5 hour. An additional 30 mL portion of water was added slowly over the 30 minutes of heated stirring. The reaction mixture was allowed to cool to room temperature. The cooled mixture was placed in an ice bath and stirred for 1.0 hour. The solid was isolated by filtration, and rinsed with a 20 mL chilled mixture of 67% water and 33% 1-propanol. The isolated solid was dried in vacuo at 35° C. overnight. The solid was identified as the propanol solvate of dirithromycin by $^1$H NMR spectroscopy.

Total yield: 77.6%

Potency: 89.9%

EXAMPLE 7

2-Propanol Solvate of Dirithromycin

A 5 g portion of dirithromycin was added to a solvent mixture comprised of 5 mL water and 23 mL 2-propanol. The solution was heated to 55° C. to allow the solid to dissolve. The reaction mixture was heated to 83° C. and allowed to boil until the reaction volume was 10 mL. Dirithromycin seed crystals were added to the mixture with stirring. The reaction mixture was allowed to cool to room temperature and 3 mL of water were added to the sample with stirring. The solid was isolated by filtration and washed with 3 washes, each of 50 ml of water. The product was dried and was identified as the 2-propanol solvate by x-ray powder diffractometry and NMR spectroscopy.

EXAMPLE 8

1-Butanol Solvate of Dirithromycin

A 5 g portion of dirithromycin was added to a solvent mixture comprised of 5 mL water and 40 mL 1-butanol. The solution was heated to boiling and allowed to boil until the reaction volume was 15 mL. The reaction mixture was cooled to room temperature with stirring. Dirithromycin seed crystals were added to the stirring mixture. The reaction mixture was stirred for 10 minutes and 40 mL of hexane was added to the reaction mixture to precipitate the solvate. The mixture was stirred for 5 minutes at room temperature. The solid was isolated by filtration and washed with 3 washes, each of 50 mL of deionized water. The sample was dried in a vacuum desiccator. The product was identified as the 1-butanol solvate by x-ray powder diffraction and NMR spectroscopy.

EXAMPLE 9

Isolation of Dirithromycin Form II From the Acetonate

A 20 g portion of non-solvated dirithromycin was added to a solvent mixture comprised of 81 mL acetone and 9 mL water. The solution was heated to about 60° C. The solution was maintained at 60° C. until the reaction volume was 35 mL. An additional 100 mL portion of water was added slowly over 1 hour. The mixture was allowed to cool to room temperature. The cooled mixture was placed in an ice bath and stirred for 1 hour. The solid was isolated by filtration, and rinsed with 25 mL of chilled solvent comprised of 67% water and 33% acetone. The solid was rinsed with a 40 mL portion of water at ambient temperature. The wet cake of acetone solvate of dirithromycin was left at ambient conditions overnight.

A 180 mL portion of water was added to the wet cake of acetone solvate. The mixture was heated to 70° C., and was stirred at 70° C. with a nitrogen purge for 4 hours. The solid was immediately isolated by filtration and rinsed with a 30 mL portion of water which had been warmed to 70° C. The isolated solid was dried in vacuo at 40° C. overnight. The solid was identified as Form II dirithromycin by x-ray powder diffractometry.

Total yield: 90.8%

Potency: 96.05%

TRS: 3.04% (Reduced from 4.53% in the non-solvated dirithromycin).

EXAMPLE 10

Isolation of Form II Dirithromycin

A 10.0 g sample of acetone solvate of dirithromycin, prepared by the method of Example 1 was added with stirring to 100 mL of water with nitrogen purge. The temperature of the reaction mixture was increased to 74° C. and stirred at about 72°–75° C. for 4 hours. The warm mixture was vacuum filtered and washed with about 35 mL of 60° C. water. The solid was dried in vacuo at 50° C. overnight. The solid was identified as Form II dirithromycin, by x-ray powder diffractometry. The total yield of the reaction was 8.74 g (87.4%).

Potency: 90.7%

Acetone: < 0.03%

The process of Example 10 was repeated with the following results:

Total yield: 8.77 g (87.7%)

Potency: 93.2%

Acetone: < 0.03%

EXAMPLE 11

Isolation of Form II Dirithromycin From Form I (water)

A 15 g portion of Form I dirithromycin was added to 150 mL water. The reaction mixture was heated to 74° C. and stirred for 4 hours at 74° C. The solid was isolated by filtration and washed with two washes, each of 40 mL of 70° C. water. The sample was dried in a vacuum oven at 25° C. for about 68 hours. The product was identified as Form II dirithromycin by x-ray powder diffractometry.

Yield: 97.5%
Potency: 96.0%
TRS: 3.8%

EXAMPLE 12

Isolation of Form II Dirithromycin from Form I (EtOAc)

A 5 g portion of Form I dirithromycin was added to 25 mL ethyl acetate. The solution was heated to 76° C. and allowed to boil until the reaction volume was about 15 mL. The reaction mixture was allowed to cool to room temperature and 20 mL of water were added to the sample with stirring. The solid was isolated by filtration and washed with three washes, each of 25 mL water. The sample was washed with one wash of heptane. The product was identified as Form II dirithromycin by x-ray powder diffractometry.

EXAMPLE 13

Isolation of Form II Dirithromycin

A 3.01 g portion of Form I dirithromycin was added to 15 mL ethyl acetate. The reaction mixture was heated to about 76° C. and the mixture was allowed to boil until the reaction volume was about 10 mL. A 20 mL portion of n-octane was added. The mixture was allowed to cool to room temperature. The solid was isolated by filtration. The sample was dried at room temperature. The product was identified as Form II dirithromycin by x-ray powder diffractometry.

Total Yield: 95%

EXAMPLE 14

The following data relates to a tablet containing 250 mg of dirithromycin Form II as the active ingredient.

|  | mg/Tablet |
|---|---|
| Core Tablet |  |
| Dirithromycin Form II | 250.0 mg |
| Magnesium Carbonate | 250.0 mg |
| Microcrystalline Cellulose | 199.6 mg |
| Sodium Starch Glycolate | 10.0 mg |
| Hydroxypropyl Cellulose | 15.0 mg |
| Croscarmellose Sodium | 10.0 mg |
| Magnesium Stearate | 12.0 mg |
| Subcoating |  |
| Hydroxypropyl Methylcellulose 2910 (E-5) | 16.21 mg |
| Polyethylene Glycol (3350) | 4.63 mg |
| Propylene Glycol | 6.95 mg |
| Benzyl Alcohol | 2.31 mg |
| Enteric Coating |  |
| Methacrylic Acid Copolymer Aqueous Dispersion (L30D) (Solids) | 48.65 mg |
| Color Mixture White T3166-WE (Solids) | 20.31 mg |
| Triethyl Citrate | 1.65 mg |
| Talc | Trace |

Core Tablets:

The lots may be prepared as a single entity or fraction thereof and all units blended as a dry mix before compression. All ingredients are security sieved. Dirithromycin (Form II), magnesium carbonate, microcrystalline cellulose, sodium starch glycolate, hydroxypropyl cellulose, and magnesium stearate are thoroughly blended in a ribbon mixer or other type of suitable mixer such as a V-blender, conical mixer, etc. The resulting powder mixture is compacted using a roller compactor or equivalent dry granulating equipment. The granulation is sized if necessary using an oscillating granulator, fitz mill or other suitable milling equipment. The sized granulation is blended with additional microcrystalline cellulose, croscarmellose sodium, and magnesium stearate in a ribbon mixer or other type of suitable mixer such as a V-blender, conical mixer, etc. After blending, the weight is checked against theoretical. The granulation is compressed on a conventional type compression machine such as a Manesty Betapress, etc. Weight checks of the core tablets are made routinely throughout the compression process and the samples are pooled for testing.

Subcoating:

The subcoating is prepared by dissolving hydroxypropyl methylcellulose 2910 (E-5), polyethylene glycol, propylene glycol and benzyl alcohol in purified water. This coating solution can be prepared using a Groen kettle, stockpot, or equivalent and a means to provide agitation such as a Lightening mixer or equivalent.

This coating solution is applied to the core tablets from above in an Accela Cora coating pan or equivalent film coating equipment. Suitable spraying systems such as the Accela-Spray II, Nordson spray unit, Graco spray unit or equivalent spraying equipment are utilized. Alternate spraying and drying cycles are used if necessary until the desired amount of coating solution has been applied.

Enteric Coating:

The enteric coating suspension is prepared by mixing methacrylic acid copolymer aqueous dispersion (L30D), color mixture white T3166-WE, and triethyl citrate with purified water. This coating suspension can be prepared using a Groen kettle, stockpot, or equivalent and a means to provide agitation such as a Lightning mixer or equivalent.

This coating suspension is applied to the subcoated tablets from above in an Accela Cora coating pan or equivalent film coating equipment. Suitable spraying systems such as the Accela-Spray II, Nordson spray unit, Graco spray unit or equivalent spraying equipment are utilized. Alternate spraying and drying cycles are used if necessary until the desired amount of coating suspension has been applied. The tablets may be finished by dusting lightly with talc (to increase the luster of the coated tablets). Only trace amounts of this polishing agent adheres to the finished tablets.

We claim:

1. A compound selected from purified Form II dirithromycin which has a typical x-ray powder diffraction pattern as follows, using a Nicolet 12V powder diffractometer, wherein d represents the interplanar spacing:

| d(Å) | d(Å) |
|---|---|
| 14.17 | 4.72 |
| 11.96 | 4.50 |
| 10.43 | 4.44 |
| 9.65 | 4.24 |
| 8.86 | 4.20 |
| 8.18 | 4.11 |
| 7.07 | 4.09 |
| 6.99 | 3.92 |
| 6.84 | 3.87 |
| 6.59 | 3.83 |
| 6.24 | 3.73 |
| 6.07 | 3.55 |

| d(Å) | d(Å) |
| --- | --- |
| 5.97 | 3.49 |
| 5.77 | 3.46 |
| 5.54 | 3.42 |
| 5.50 | 3.33 |
| 5.45 | 3.17 |
| 5.13 | 3.11 |
| 5.11 | 2.96 |
| 4.84 | 2.83 |
| 4.75 | 2.74 |
|  | 2.57. |

2. A solid pharmaceutical formulation comprising a pharmaceutically effective amount of a compound of claim 1, as an active ingredient associated with one or more pharmaceutically acceptable excipients.

3. A formulation of claim 2 which contains a basic excipient.

4. A formulation of claim 3 wherein the basic excipient is magnesium carbonate.

5. A formulation of claim 2 in the form of tablet.

* * * * *

UNITED STATES PATENT AND TRADEMARK OFFICE
CERTIFICATE OF CORRECTION

PATENT NO. : 5,556,839

DATED : September 17, 1996

INVENTOR(S) : James M. Greene, et al.

It is certified that an error appears in the above-identified patent and that said Letters Patent is hereby corrected as shown below:

Column 12, line 50, please delete the phrase " compound selected from".

Signed and Sealed this

Fifth Day of August, 1997

Attest:

Attesting Officer

BRUCE LEHMAN

Commissioner of Patents and Trademarks